United States Patent [19]

Sabater et al.

[11] Patent Number: 4,788,442
[45] Date of Patent: Nov. 29, 1988

[54] DEVICE FOR DETECTING INCIPIENT TEARS ON A SHEET DURING MANUFACTURE

[75] Inventors: Jacques Sabater, Gif/Yvette; Serge Bauduin, La Tronche, both of France

[73] Assignee: Centre Technique De L'Industrie Des Papiers, Cartons Et Celluloses, Grenoble, France

[21] Appl. No.: 75,747

[22] PCT Filed: Dec. 23, 1986

[86] PCT No.: PCT/FR86/00442
  § 371 Date: Jun. 30, 1987
  § 102(e) Date: Jun. 30, 1987

[87] PCT Pub. No.: WO87/04248
  PCT Pub. Date: Jul. 16, 1987

[51] Int. Cl.[4] ............................................. G01N 21/84
[52] U.S. Cl. ..................................... 250/572; 356/430
[58] Field of Search .............. 250/562, 563, 571, 572; 356/239, 430, 431, 438

[56] References Cited

U.S. PATENT DOCUMENTS

| | | | |
|---|---|---|---|
| 3,710,129 | 1/1973 | Gibson | 250/572 |
| 3,783,296 | 1/1974 | Blevins | 250/572 |
| 3,835,332 | 9/1974 | Bridges | 356/430 |
| 3,840,302 | 10/1974 | Brunton et al. | 356/430 |
| 4,682,038 | 7/1987 | Focke | 250/571 |

Primary Examiner—David C. Nelms
Assistant Examiner—Stephone B. Allen
Attorney, Agent, or Firm—Parkhurst, Oliff & Berridge

[57] ABSTRACT

Device for detecting insipient cracks or tears on the edges (4) of a moving sheet (5), of the type comprising:
  a light source (6),
  and a receiving cell for picking up the light transmitted by the source (6) through the sheet (5) moving between the source (6) and the cell,
characterized in that:
  on the one hand, the light source (6) is a laser source;
  and on the other hand, the receiving cell (17) is an optoelectronic cell placed in such a way that the solid angle under which the serviceable surface of said cell (17) or of its image by an optical system, can be seen from the sheet, is less than 0.01 steradian.

10 Claims, 1 Drawing Sheet

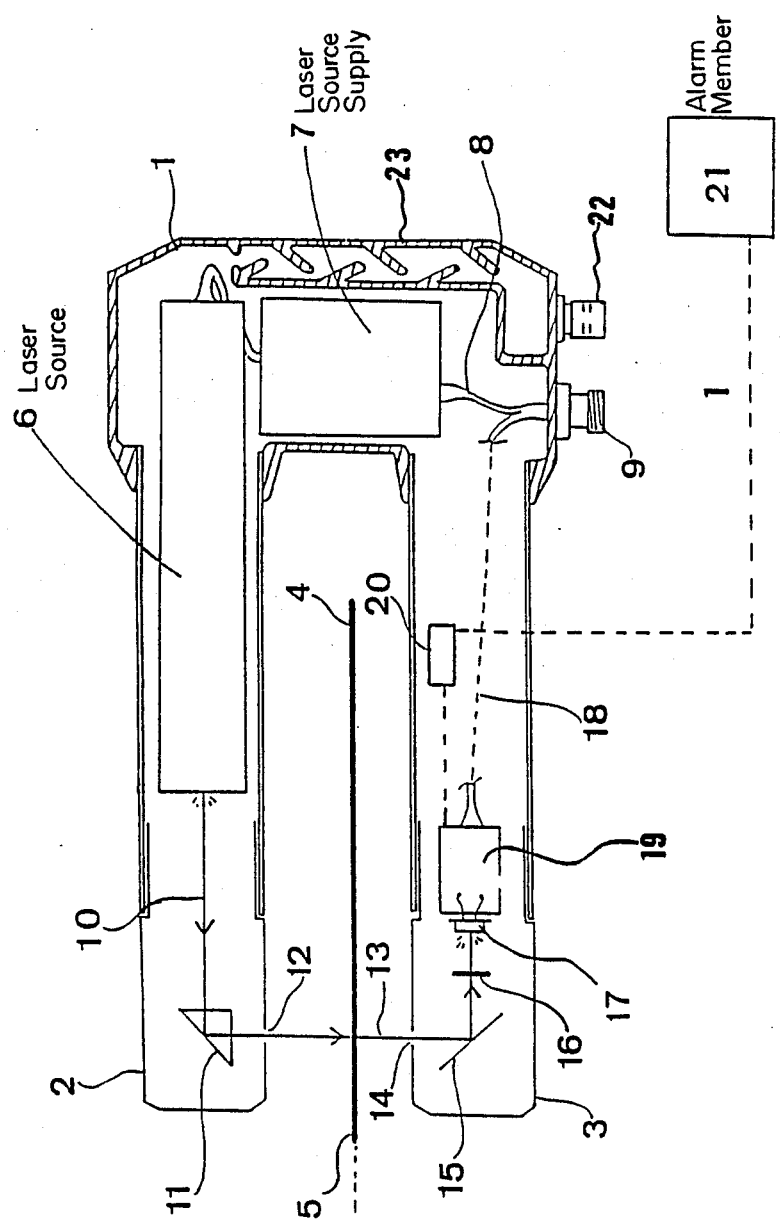

DEVICE FOR DETECTING INCIPIENT TEARS ON A SHEET DURING MANUFACTURE

BACKGROUND OF THE INVENTION

The present invention relates to a device for detecting insipient tears on the edges of a sheet during manufacture, such as for example a sheet of paper, cardboard or the like.

The manufacture of a sheet of paper is carried out on a papermachine permitting successively the shaping, drying and rolling of the sheet. Throughout the manufacture, the said sheet is subjected to a large number of stresses due either to shrinkages during drying, or to variations in the moving speed of the various cylindrical members provided for driving and drying the sheet, the speed of which members is difficult to control. Also, the sheet of paper very often undergoes a surface wetting treatment which temporarily makes it delicate, and even more so as the manufacturing speeds are generally around several hundreds of meters per minute.

Under these conditions, it is easy to understand that this material of which the thickness is but a few tens of microns and which is relatively fragile, can suffer tears and even cracks which interfere with the manufacturing program and in the end prove very expensive.

It is therefore important to be able to detect as accurately as possible any incipient tears occurring on the edge of a sheet during manufacture and which are the forerunning sign of a forthcoming tear.

Very simple devices are already known, these devices being constituted of a light source, generally a filament lamp, and of a cell placed on the other side of the sheet. The sheet of paper then moves between the light source and the cell which, at that moment picks up the light transmitted through the sheet. As long as the sheet of paper passes normally between the light source and the cell, the transmitted light intensity is low. On the contrary, when there is an insipient tear, the cell receives all the light intensity emitted by the source, this triggering alarm means.

Although this device is widely used, it has however many drawbacks. First of all, the light emitted by the source spreads in all directions. As a result, the quantity of light received in one point of the sheet is very small, which affects the detection. Also, the detection cells are affected by the surrounding light radiations, since their receiving angle is too wide. Finally, with time, the detection device becomes dirty, since fibers and filling materials deposit on the optical surfaces provided for allowing the light beam to pass through, and then the device becomes unusable.

In order to obtain the best possible conditions of detection, it would then be necessary for the quantity of light received by the cell to be very small when the sheet of paper passes between the source and the cell, and very large when the light emitted by the source reaches directly the cell, which has not been possible heretofore.

SUMMARY OF THE INVENTION

The device according to the invention overcomes these disadvantages. This device for detecting insipient tears on the edge of a moving sheet of paper, of the type comprising:
a light source, and
a receiving cell for picking up the light through the sheet moving between the cell and the source,
is characterized in that:
first the light source is a laser source, and
second, the receiving cell is an optoelectronic cell placed in such a way that the solid angle under which the serviceable surface of said cell or its image through an optical system can be seen from the sheet of paper, is less than 0.01 steradian.

In other terms, the invention consists in combining the laser source as light source with an optoelectronic receiving cell, with the condition that the solid angle under which the serviceable surface of said cell can be seen from the sheet of paper, is less than 0.01 steradian.

Indeed, it has been found that if said solid angle is more than 0.01 steradian, the quantity of light diffused by the sheet and received by the cell, namely the quantity of light diffused in said solid angle, would be greater and consequently the difference of the light flux received by the cell when there is an insipient tear and when there is not, would be lower. This, then, would affect the accuracy of the measurement.

In practice, the bottom value results from the surface of the cell which is about a few square millimeters.

It has also been found that, if another light source is used instead of a laser source, then the advantage of the coherence of space of the light beam, and in particular the advantage of a considerable difference of the light beam received by the cell in the presence of an insipient tear, would be lost.

Since the light beam of the laser source is perfectly cylindrical, the moving sheet is lit in only one point. As a result, the examined area receives all the light emitted by said source. Thus, when there is an insipient tear on the sheet, the light beam encounters no obstacle and then the cell receives all the light emitted by the source. On the contrary, when the sheet is undamaged, the transmitted light is diffused in all directions comprised in a solid angle cone of $\pi$ (pi) steradians.

If the sheet is at a distance d from the cell or from its optical image, and if the serviceable surface of the cell is S, the solid angle under which the cell or its optical image is seen from the sheet is $S/d2$. The quantity of light picked up being proportional to the solid angle, the cell then will only receive $(S/d2)/\pi$ of the quantity of light diffused.

If in one example of embodiment corresponding to practice, $S=5$ mm2 and distance $d=5$ cm, the solid angle under which the cell is seen from the sheet is 0.003 steradian and the cell then only receives less than one thousandth of the light diffused by the sheet.

The device according to the invention therefore permits the detection with very great accuracy of insipient tears in a moving sheet, and in particular in a sheet of paper being manufactured.

Advantageously, in practice:
the laser source is a gas laser or a semi-conductor laser;
the optoelectronic cell is a cell with very small surface, i.e. of a few square millimeters;
a diaphragm may be placed in front of the optoelectronic cell so as to reduce the serviceable surface of the cell to the wanted size;
the serviceable surface of the optoelectronic cell is, as already indicated, the smallest possible so as to have a very accurate device but nevertheless larger than the size of the light spot on the sheet of paper, increased by the divergence of the laser beam;

preferably, said surface is such that the solid angle under which said cell, or its image is seen by way of an optical system, from the sheet of paper, is less than 0.01 steradian and advantageously is 0.003;

dry compressed air is sent into the device at the level of the orifices designed to allow the light beam through; thus, owing to the excess pressure, the formation of deposits of fibers or of filling materials on the optical surfaces, is avoided.

According to a preferred embodiment, the device according to the invention is constituted of a casing shaped as a U of which the two branches contain respectively the laser source and the optoelectronic cell. The laser source supply is contained in that part of the casing joining the two branches of the U. Said casing comprises a supply of dry compressed air which is discharged through the orifices provided for letting the light beam through. The optical surfaces are thus sheltered from surrounding dust. The compressed air is also used simultaneously for cooling the laser tube and its supply. To prevent sharp angles which could cause breakages in the sheet when untimely vibrations occur, the two branches of the U are tubular.

In order to weaken the effect of ambient light radiations, an extra diaphragm is inserted between the sheet of paper and the cell or the image thereof by an optical system.

BRIEF DESCRIPTION OF THE DRAWING

The manner in which the invention can be produced and the advantages deriving therefrom will be more readily understood on reading the following example of embodiment given by way of indication and non-restrictively, with reference to the one and only figure which is a cross-sectional view of one advantageous embodiment of the insipient tear detection device according to the invention.

DESCRIPTION OF THE PREFERRED EMBODIMENTS

This insipient tear detection device essentially comprises a casing (1) on which are fitted two parallel tubular branches (2, 3) between which passes the edge (4) of a moving sheet of paper (5).

The assembly (1, 2, 3) therefore has the general shape of a U.

The upper branch (2) contains a laser source (6) for example a helium-neon laser, supplied from an appropriate member (7) connected via connections (8) to an admission provided on the casing.

Said laser (6) emits a ligh beam (10) which is reflected by a mirror type prism (11) onto the sheet (5) through opening (12). The transmitted beam (13) then goes through another opening (14) provided in the parallel branch (3) in order to be reflected onto a mirror (15), and it goes through a diaphragm (16) and reaches an optoelectronic cell (17) such as a silicon cell. Said silicon cell is electrically supplied by a connection (18) which is also connected with admission (9). Cell (17) is connected to an electronic card (19) which is in turn connected via a power relay (20) to one or more alarm members (21), such as an indicator light, a bell or a display counter.

In the illustrated example, the solid angle is near to 0.002.

The casing (1) is also provided with a compressed air admission (22) connected to a source (not shown). The compressed air which goes through baffle means (23) is used, on the one hand, for cooling the laser source (6) and on the other hand, while being discharged through (12) and (14), for cleaning said two orifices provided for the passage of the laser beam (10, 13), thereby preventing the dirtying of the optical elements (11, 15, 17).

In the case of a crack or a tear, the quantity of light received by the cell (17) suddenly increases. As a result, and because of the presence of the electronic card (19), alarm (21) is triggered. The conductor then marks the continuously moving sheet in order to locate the fault.

This detection device is particularly advantageous:

first, because of its simple structure which comprises no moving piece, and second, because of its simplicity of design and of positioning and because of its reliable operation.

It is therefore perfectly adapted for papermaking machines.

We claim:

1. A device for detecting insipient cracks or tears on the edges of a moving sheet comprising:
   a laser light source, and
   an opto-electronic receiving cell for receiving the light transmitted by the laser light source through the sheet moving continuously between the laser light source and the receiving cell, wherein the receiving cell is placed whereby a solid angle under which the serviceable surface of said cell, or of an image of the serviceable surface of said cell produced by an optical system, can be seen from said moving sheet of paper is less than 0.01 steradian.

2. A device according to claim 1, wherein the laser source is a gas laser.

3. A device according to claim 1, wherein the laser source is a semi-conductor laser source.

4. A device according to claim 1, wherein a diaphragm is inserted between the moving sheet and the cell or the image thereof via an optical system so as to reduce the serviceable surface of said cell to a desired size.

5. A device according to claim 1, wherein said solid angle is near 0.003 steradian.

6. A device according to claim 1, wherein said light source and said receiving cell are respectively contained in each of two branches of a U-shaped assembly, and each of said branches are joined to a casing.

7. A device according to claim 6, wherein said casing comprises a supply of compressed air for cooling said light source and keeping, by an excess of pressure, optical surfaces in the device in a clean condition, said compressed air flowing through orifices provided for the passage of the light transmitted by the laser light source.

8. A device for detecting insipient cracks or tears on the edges of a moving sheet consisting of a U-shaped assembly, comprising two branches which are joined to a casing said branches encasing opposingly disposed a laser source and a receiving cell for receiving the light transmitted by the laser source through the sheet moving continuously between the branches of the U-shaped assembly, wherein said receiving cell is an optoelectronic cell comprising a diaphragm inserted between the moving sheet and the cell, or the image thereof via an optical system, and
   said receiving cell being placed whereby the solid angle under which the serviceable surface of said cell, or of an image of the serviceable surface of said cell produced by an optical system, can be seen from the moving sheet is less than 0.01 steradian.

9. A device according to claim 8, wherein said casing comprises a supply of compressed air for cooling the light source and keeping, by an excess of pressure, optical surfaces in the device in a clean condition, said compressed air flowing through orifices provided for the passage of the light transmitted by the laser source.

10. A device according to claim 8, wherein said solid angle is approximately 0.003 steradian

* * * * *